(12) United States Patent
Eide

(10) Patent No.: US 10,485,581 B2
(45) Date of Patent: Nov. 26, 2019

(54) DEVICE FOR INTRODUCING AND MAINTAINING A PORT IN AN UMBILICAL VESSEL

(71) Applicant: Terje Eide, Blommenholm (NO)

(72) Inventor: Terje Eide, Blommenholm (NO)

(*) Notice: Subject to any disclaimer, the term of this patent is extended or adjusted under 35 U.S.C. 154(b) by 36 days.

(21) Appl. No.: 15/560,741

(22) PCT Filed: Mar. 18, 2016

(86) PCT No.: PCT/NO2016/050052
§ 371 (c)(1),
(2) Date: Sep. 22, 2017

(87) PCT Pub. No.: WO2016/153357
PCT Pub. Date: Sep. 29, 2016

(65) Prior Publication Data
US 2018/0055537 A1    Mar. 1, 2018

(30) Foreign Application Priority Data

Mar. 25, 2015   (NO) .................................. 20150362

(51) Int. Cl.
| | | |
|---|---|---|
| *A61B 17/34* | (2006.01) | |
| *A61M 39/10* | (2006.01) | |
| *A61B 5/15* | (2006.01) | |
| *A61M 39/02* | (2006.01) | |

(Continued)

(52) U.S. Cl.
CPC .... *A61B 17/3423* (2013.01); *A61B 5/150038* (2013.01); *A61B 5/150992* (2013.01); *A61B 17/122* (2013.01); *A61B 17/1227* (2013.01); *A61M 25/04* (2013.01); *A61M 39/0208* (2013.01); *A61M 39/1011* (2013.01); *A61B 2017/345* (2013.01); *A61B 2017/347* (2013.01); *A61B 2017/3456* (2013.01); *A61B 2017/3488* (2013.01); *A61B 2503/045* (2013.01);
(Continued)

(58) Field of Classification Search
CPC ...... A61B 2017/345; A61B 2017/3484; A61B 2017/3486; A61B 2017/3488; A61B 5/150038; A61M 2039/0202; A61M 2240/00
See application file for complete search history.

(56) References Cited

U.S. PATENT DOCUMENTS

| | | |
|---|---|---|
| 4,585,437 A | 4/1986 | Simms |
| 4,642,101 A | 2/1987 | Krolikowski et al. |
| 5,370,627 A | 12/1994 | Conway |

(Continued)

FOREIGN PATENT DOCUMENTS

| | | |
|---|---|---|
| CN | 202235583 | 5/2012 |
| CN | 103127600 | 6/2013 |

(Continued)

OTHER PUBLICATIONS

International Search Report dated Jan. 17, 2017, in corresponding PCT Application No. PCT/NO2016/050052.

*Primary Examiner* — Laura A Bouchelle
(74) *Attorney, Agent, or Firm* — Buchanan Ingersoll & Rooney PC

(57) ABSTRACT

The present invention relates to devices and processes for introducing and maintaining a port in an umbilical vessel and uses thereof. Further the invention relates to kits comprising said device and the uses thereof.

8 Claims, 6 Drawing Sheets

(51) Int. Cl.
*A61B 17/122* (2006.01)
*A61M 25/04* (2006.01)

(52) U.S. Cl.
CPC .............. *A61M 2039/0202* (2013.01); *A61M 2039/0205* (2013.01); *A61M 2240/00* (2013.01)

(56) References Cited

U.S. PATENT DOCUMENTS

| | | | | |
|---|---|---|---|---|
| 5,575,795 | A | | 11/1996 | Anderson |
| 6,053,902 | A | * | 4/2000 | Bestetti ................ A61M 25/04 604/174 |
| 6,908,447 | B2 | * | 6/2005 | McWeeney ........... A61F 2/0022 604/9 |
| 7,214,228 | B2 | * | 5/2007 | Crabtree ............ A61B 17/3403 604/506 |
| 8,105,308 | B2 | * | 1/2012 | Ghodsian .......... A61M 39/0247 604/500 |
| 2012/0253279 | A1 | * | 10/2012 | Thorp ................ A61B 5/15003 604/96.01 |
| 2014/0046213 | A1 | | 2/2014 | Benbunan |

FOREIGN PATENT DOCUMENTS

| | | |
|---|---|---|
| FR | 1 512 435 | 12/1966 |
| FR | 2609635 | 7/1988 |

\* cited by examiner

DEVICE FOR INTRODUCING AND MAINTAINING A PORT IN AN UMBILICAL VESSEL

CROSS-REFERENCE TO RELATED APPLICATIONS

This application is a U.S. National Phase Application pursuant to 35 U.S.C. § 371 of International Patent Application No. PCT/NO2016/050052, filed on Mar. 18, 2016, and published as WO 2016/153357 on Sep. 29, 2016, which claims the benefit of Norway Patent Application No. 20150362, filed on Mar. 25, 2015, the entireties of which are incorporated herein by reference for all purposes.

FIELD OF INVENTION

The present invention relates to devices and processes for introducing and maintaining a port in an umbilical vessel. Further the invention relates to kits comprising said device and the uses thereof.

BACKGROUND OF THE INVENTION

Umbilical venous catheterization is a common procedure in the management of sick neonates. These catheters are commonly used for the administration of fluids, nutrition and medications, blood gas monitoring, and exchange transfusions (M. Butler O'Hara, C. J Buzzard, L. Reubens, M. P McDermot, W. DiGrazio and C. T. D'Angio. A is randomized trial comparing long-term and short-term use of umbilical venous catheters in premature infants with birth weights of less than 1251 grams, Pediatrics 2006; vol 118; no 1, p 25-35).

The umbilical cord comprises two umbilical arteries and one umbilical vein embedded in mucous connective tissue, so called Whartons jelly, in addition to endodermal remnants of the allantois, extending the length of the cord in humans. The cord is enveloped in a simple epithelium of amniotic derivation. Both the arteries and vein differ from the corresponding vessels in the body in that the arteries are carrying oxygen poor blood while the vein is carrying oxygen rich blood. Thus there are differences in the anatomy. Accordingly the arteries exhibits a comparatively thick muscularis, with intermingling circular, longitudinal and obliquely smooth muscle fibers. An internal elastic lamina is present, distinguishing the vein from the accompanying arteries. The mucous connective tissue is a form of loose connective tissue. The vessels have a helical course which impedes compressing of the vessels and make the cord stronger.

Immediately following birth, that is at 1, 5 and 10 minutes, the neonates are subjected to establishment of an Apgar score to judge the condition of the neonate. The score comprises an evaluation of the condition of the child within five different areas, such as heart rate, breathing effort, muscle tone, reflexes and skin color. Each condition is scored from 0-2 which is added to give a total score of 0-10. The neonate is retested after 5 minutes and if necessary subjected to further tests at 5 minutes intervals. The first test might give a low score which is normalized after 5 minutes. Normal score is regarded to be 7 and above. A total score of 3 or less is indicative of a critical condition, often combined with bluish color of the skin. This is named birth asphyxia due to insufficient respiration and circulation caused by problems in the umbilical cord or infection. In such case it is necessary within 5 minutes to establish free respiratory passages and restore normal circulation with fluid and/or medicaments. The umbilical vein is in the art regarded to be the most suitable port to inject adequate amounts of fluid into the central circulation of the neonates in order to reestablish normal circulation as quickly as possible.

Due to the anatomy and course of the umbilical vessels and that the cord of a neonate normally is slippery and compliant, the establishment of venous access through the umbilical vein is regarded technically difficult. When the neonate is critically ill, it is necessary to open up an infusion port within 5 minutes. It is often difficult to position a catheter 3-5 cm beyond the muco-cutaneous junction which is necessary to avoid is malpositioning of the catheter in the portal circulation and the accompanying possibility of hepatic necrosis. An established method is to insert the tips of an iris forceps into the vein and force the mouth of the vein open and insert the tip of the catheter.

Several methods to catheterize umbilical vessels are published in the art (US Patent Application Publication No 2009/062774, U.S. Pat. Nos. 8,105,308 and 4,585,437). U.S. Pat. No. 4,585,437 regards an improved device for introducing an umbilical artery catheter into an infant. The device consists of a funnel-like body with a handle-like member at the enlarged open end. At the end inserted into the arterial system, the small end of the funnel-like body consists of a plurality of prong-like nibs. The small end at the distal end of the prong-like nibs is bulbous-like and serves to prevent the device from being extruded from the arterial system once it is in place. U.S. Pat. No. 8,105,308 provides a method and an apparatus for catheterization of umbilical vessels in a newborn wherein the tube will remain permanently at the location. The method comprises inserting, with a guiding member, a tube into an umbilical vessel in an umbilical cord prior to occlusion of the umbilical vessel, wherein the tube is configured to have dimensions so that the tube remains in a fixed position within the umbilical vessel both prior to and after the occlusion of the umbilical vessel. The tube has a first end and a second end wherein the second end is closed and a valve operably connected to the first end of the tube and configured to provide access to the interior of the tube to the guiding member, wherein the tube is impermeable, removing the guiding member from the tube and clamping the umbilical cord, whereby the tube is permanently placed within the umbilical vessel of the newborn. US Patent Application Publication No 2009/062774 provides an invention relating to a device for introducing a silicone catheter by the umbilical route. The introducing device comprises polyurethane catheter in which the silicone catheter can slide, and a rectilinear and rigid tube which is made of stainless metal and is shorter than the catheter and whose internal diameter is adapted to the external diameter of the silicone catheter in order to allow the silicone catheter to slide in the metal tube, while preventing entry of air between them. This metal tube is introduced into the proximal end of the polyurethane catheter and fixed to said catheter in such a way as to prevent entry of air between them. This invention applies in particular to the catheterization of premature babies or neonates.

None of the above described methods and devices prove useful to apply when reviving critically ill neonates of mammalian origin, especially when the time factor is critical. Usually such catheterization is performed with long intervals by the skilled person in the art who therefore lacks training in the procedure. Thus there is a need in the art for is an improved method which can be performed by the skilled person without the need for repetitive training.

Thus the object of the present invention is to provide a device and method for introducing and maintaining a port in an umbilical vessel in mammalian neonates. The device is easily positioned by health personell normally attending the childbirth, such as doctors, midwifes and nurses. No specialized skills and particular experience are required.

SUMMARY OF THE INVENTION

According to the present invention a first aspect relates to a device for introducing and maintaining a port in an umbilical vessel, comprising a cannula (1) equipped with a bulbous-like body (2) at the distal end, one or more anchors (3) attaching the device to the vessel, a connecting part (4) for connecting catheters, syringes and the like in the proximal end, and optionally a clamp (5) closing the umbilical cord. In a preferred embodiment of the invention, the clamp is present.

Another aspect of the invention relates to a process for introducing and maintaining a port in an umbilical vessel.

Yet another aspect the invention relates to a kit for umbilical vessel catheterization.

Further improved devices, processes and kits have the features mentioned in the dependent claims.

BRIEF DESCRIPTION OF THE FIGURES

Preferred embodiments of the present invention will now be illustrated in more detail with reference to the accompanying figures.

DETAILED DESCRIPTION OF THE INVENTION

Figure 1:
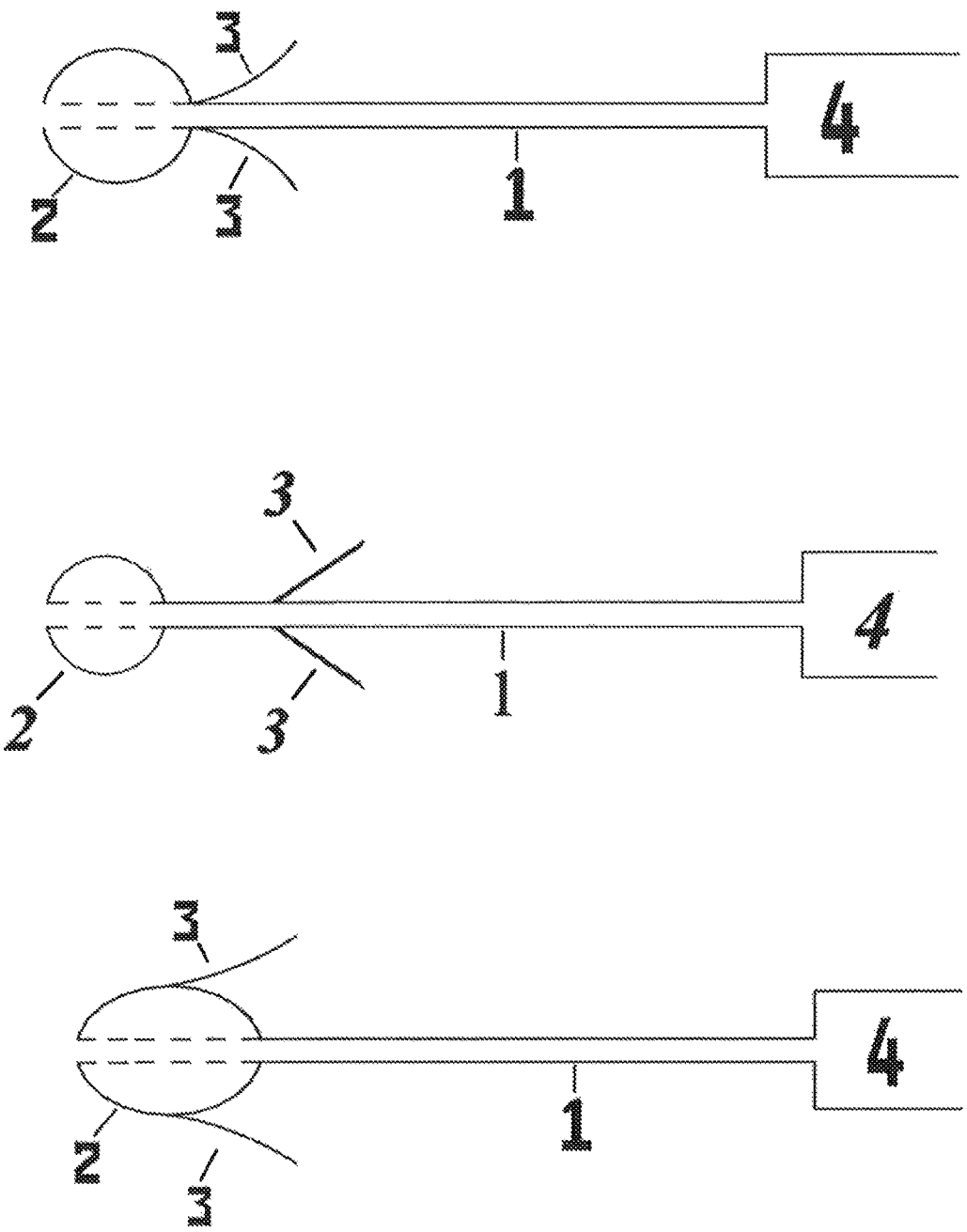
FIG. 1 shows a cross section of a first embodiment of the invention wherein the device comprises a cannula (1) equipped with a bulbous-like body (2) at the distal end, anchors (3) attaching the device to the vessel, and a connecting part (4) for connecting catheters, syringes and the like in the proximal end. Upper panel shows an embodiment of the device wherein the anchors (3) are placed at or near the proximal basis of the bulbous-like body. Middle panel, shows an embodiment of the device wherein the anchors (3) are placed in distance from the bulbous like body. Lower panel, shows a cross section of a further embodiment of the device according to the invention wherein the anchors (3) are formed as an integrated part of the bulbous-like body (2).

Umbilical vessel catheterization is a common procedure in the management of sick neonates. It is of outmost importance to have safe and easy procedures ensuring rapid access to a port for infusion of fluids and medications and aspiration of blood.

Neonates not responding to basic resuscitation are in need of advanced cardio-pulmonary-resuscitation (CPR). This necessitates intravenous injection of fluids and medication and blood samples to be taken.

In this context infusion and injection is used interchangeably.

State of the art method is to use an iris forceps to open or stretch apart the open entrance to the umbilical vessel and hold it open. Thereafter an umbilical catheter, umbilical venous catheter (UVC) allowing fluid and medicaments to be given or an umbilical artery catheter (UAC) allowing blood to be taken are inserted. Inserting such catheters in the umbilical vessels are regarded technically difficult and any inexperienced person inserting it can increase the difficulty, as there is no support in the tissue of the umbilical cord. Thus, the procedure may become too time consuming.

Thus, there is a need in the art for new devices and improved procedures for umbilical vessel catheterization.

By the present invention a new device has been provided making the umbilical vessel catheterization fast, safe and easy. The new device is applied outside the baby using the fetal route. Thus there is no need of advancement under the baby's skin which is a challenge and a potential hazard. An additional benefit is that the device is easily positioned even in the hands of unexperienced doctors, midwifes and nurses, i.e. personell normally attending the childbirth, and advanced cardio-pulmonary-resuscitation (CPR) may be given to newborns within a minute in situations wherein time is a critical factor.

The present invention relates to a device for introducing and maintaining a port in an umbilical vessel, comprising a cannula (1) equipped with a bulbous-like body (2) at the distal end (head), one or more anchors (3) attaching and securing the device to the vessel (middle part), and a connecting part (4) for connecting catheters, syringes and the like in the proximal end. The device may further be equipped with a clamp to further attach and anchor the umbilical cord and prevent leakage and backflow.

The umbilical vessel may be the umbilical vein or one of the umbilical arteries. The port may be an infusion port or an aspiration port.

The device according to the invention serves as a connector avoiding direct catheterization using state of the art umbilical artery catheter (UAC) or umbilical venous catheter (UVC). The device is safe and rapidly inserted into an umbilical vessel where after currently available catheters or syringes or the like can be connected for infusion of fluids or medicaments or for blood samples to be taken.

The dimensions of the device may vary. However, the dimensions must be suitable for the purpose of introducing a port in the umbilical cord of the neonates, either full-term or premature babies.

The cannula 1 extends through the lengths of the device and is preferably a central cannula. The internal diameter of the cannula is ranging from about 0.5-3 mm, preferably about 1-2 mm, more preferably about 2 mm. The cannula may be made of any suitable material having sufficient rigidity and which is patient compatible. Examples of suitable materials are non-toxic materials well known to be used in medical devices such as metals and polymers. Examples of suitable non-toxic metals are stainless steel and titanium. Examples of suitable non-toxic polymers are polypropylene, polyethylene, polyurethane, polyvinylchloride, Teflon and silicon.

According to one embodiment, the cannula may be a cable-like cannula comprising two or more cannulas running together to form a single assembly. The external diameter of the cable-like cannula is limited upwards by the size of the lumen of the vessel wherein the cable-like cannula is to be introduced.

The bulbous-like body (2) is located at the distal end of the device. The bulbous-like body has at least two functions which solves current challenges. First, it prevents the cannula from perforating or damaging the vessel wall. Second, the bulbous-like body serves as a guidance means, making the positioning of the cannula safe and easy.

The bulbous-like body may be configured as a spherical, spherical-like, conical, conical-like, tapered square or edged body or any other geometrical configuration forming a body preventing perforation or damage of the umbilical vessel. An impression may be made in the bulbous-like body, encircling the bulbous-like body, wherein the clamp, if present, fits into in closed position.

According to preferred embodiments, the bulbous-like body is spherical-like or conical. Preferably, the total diameter of the bulbous-like body should not exceed about 6 mm. The cannula extends through the bulbous-like body leaving an orifice of at least 2 mm.

The bulbous-like body may be made of any material suitable for the purpose and which is patient compatible. Examples of suitable materials are non-toxic materials well known to be used in medical devices such as different polymers and metals, revealing soft and flexible to hard and non-flexible designs. Examples of suitable non-toxic polymers are polypropylene, polyethylene, polyurethane, polyvinylchloride, Teflon and silicon. Examples of suitable non-toxic metals are stainless steel and titanium.

The at least one anchor (3) may have any geometrical configuration as long as it anchors, i.e. attaches and secures the positioning of the device in the vessel and thus prevents dislocation. The anchor may be in form of needle-shaped anchors, pins, spikes, nails, or tapered flattened or rounded extension. Preferably the anchors are facing backwards. Said anchors are straight or may also be curved like a hook. The anchor will perforate the vessel wall, holding the device in position and preventing the device exuding the vessel. The anchor may anchor the umbilical vessel wall internally or externally to attach and secure the position of the device.

The anchors may be formed as an integrated part of the bulbous-like body or separate as illustrated in FIG. 1. If separate it may be placed at or near the proximal basis of the bulbous-like body branching off from the cannula preferably pointing backwards i.e. in proximal direction. In this context, the term "near" is to be understood as a distance of 0-10 mm. The anchor may also be placed anywhere along the length of the cannula.

Figure 2:
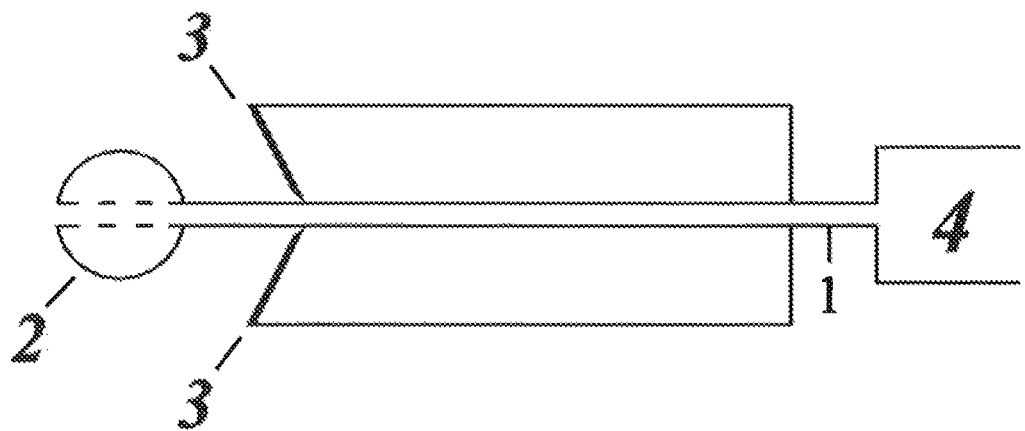
FIG. 2 shows a cross section of a further embodiment of the device according to the invention wherein the anchors (3) branches off from the proximal end of the device extending along the cannula and curve back into a hook member to perforate the umbilical vessel wall externally Upper panel shows a closed position is shown. Lower panel shows a further embodiment wherein the external diameter of the cannula (1) is expanded (1') over a portion of the cannula in the region wherein the free end of the hook abut the transition region between the expanded and non-expanded portion.
Figure 2:
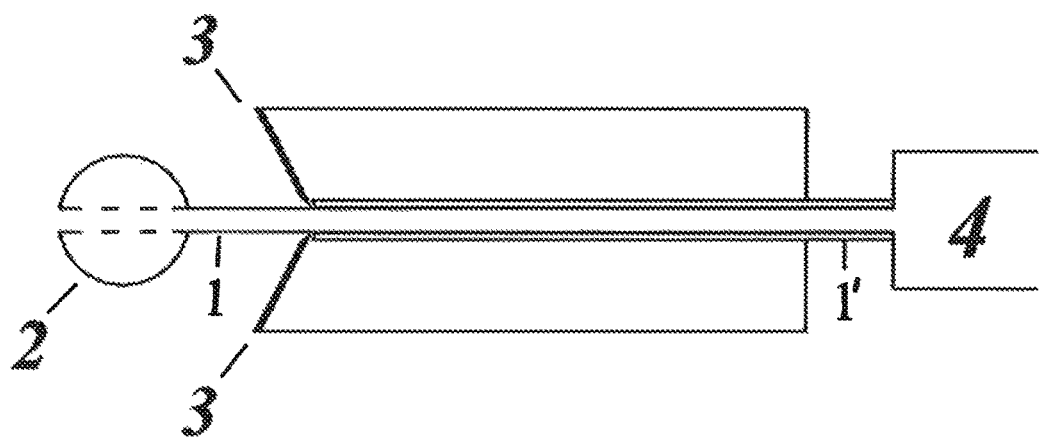
Figure 3:
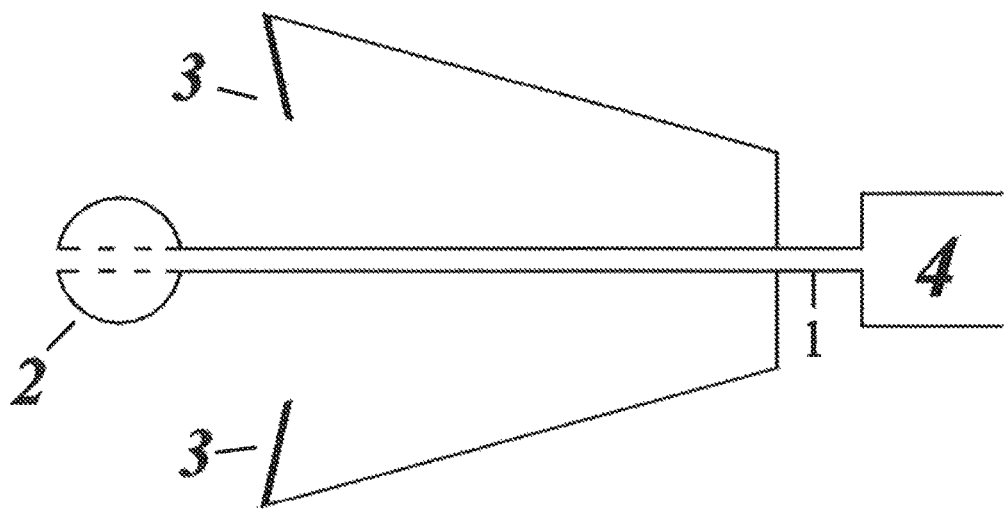
FIG. 3 upper panel shows an open position of the device according to the invention wherein the anchors (3) extend along the cannula and curve back into a hook member to perforate the umbilical vessel wall externally. Lower panel shows an embodiment wherein the device is equipped with a locking ring (3') to be moved forward to lock the anchors.
Figure 3:
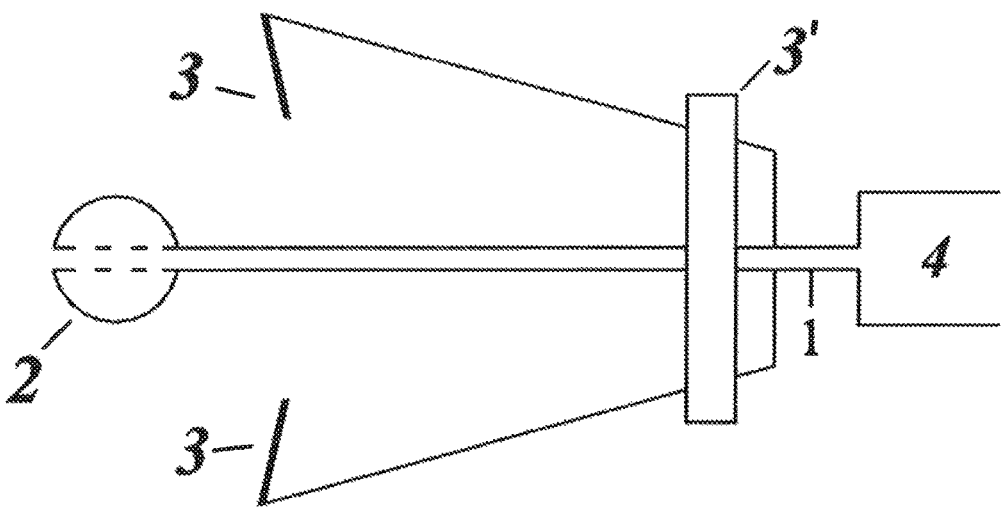

The anchors branching off from the cannula may also extend along the cannula and curve back into a hook member to perforate the umbilical vessel wall externally as illustrated in FIGS. 2 and 3. The free end of the hook points in inward direction. In an embodiment, the external diameter of the cannula (1) is expanded (1') over a portion of the cannula in the region wherein the free end of the hook abut the transition region between the expanded and non-expanded portion. Said anchor may be of any suitable length. In a further embodiment, the device may be equipped with a locking mean (3'), preferably a locking ring to be moved forward to lock the anchors. Said locking mean is well known in the art. In the above embodiments, the cannula is introduced into the vessel, the vessel wall is located in-between the cannula and the anchors which attach and perforate the umbilical vessel wall from outside.

The number of anchors may vary from at least one to a plurality of anchors. In the case of plural anchors, said anchors are preferably tiny needle-like anchors surrounding the circumference of the cannula. According to one embodiment, the number of anchors vary from 2-6, preferably 2-4, most preferably 2-3. The anchors are preferably distributed evenly around the circumference of the cannula.

The connecting part (4) at the proximal end comprises means well known in the art, such as the well-known and international standardized connecting means e.g. the connecting means identified "Luer-Lock".

Optionally, the device comprises a clamp (5) to further attach and anchor the umbilical cord. In case of infusion of fluids or medicaments, the clamp prevents backflow causing leakage and ascertains that all fluids and medication enters the body of the newborn. Thus, the volume of fluid and dosage of medicaments administered to the newborn is completely controlled.

Figure 4:
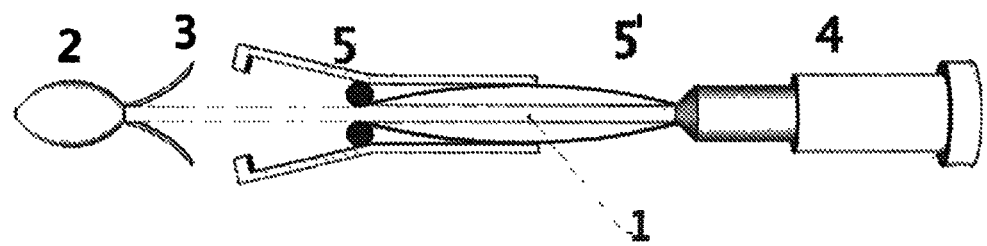
FIG. 4 shows a further embodiment of the device according to the invention wherein the device is further equipped with a spring-loaded (5') clamp (5) configured as a clothespin closing the umbilical cord. Upper panel shows an open clamp, lower panel shows a closed clamp.
Figure 4:
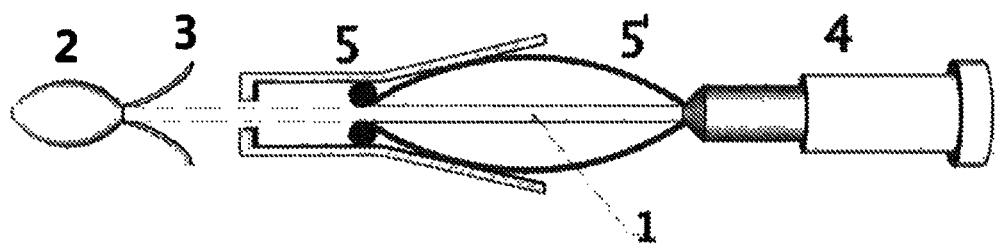

The clamp is a fastening mean well known in the art. The clamp may be configured as any suitable geometrical configuration. Preferably, the clamp is configured to serve also as a holding means for the person inserting the device. In preferred embodiments the clamp (5) is spring-loaded (5'). The spring may be of any suitable configuration well known in the art. Said spring-loaded clamp may be configured as a clothespin and is preferably a self-closing clamp as illustrated in FIG. 4. In other preferred embodiments, the clamp is not spring-loaded.

The clamp may also be equipped with anchors perforating the entire umbilical cord externally, further securing the positioning of the device.

Figure 5:
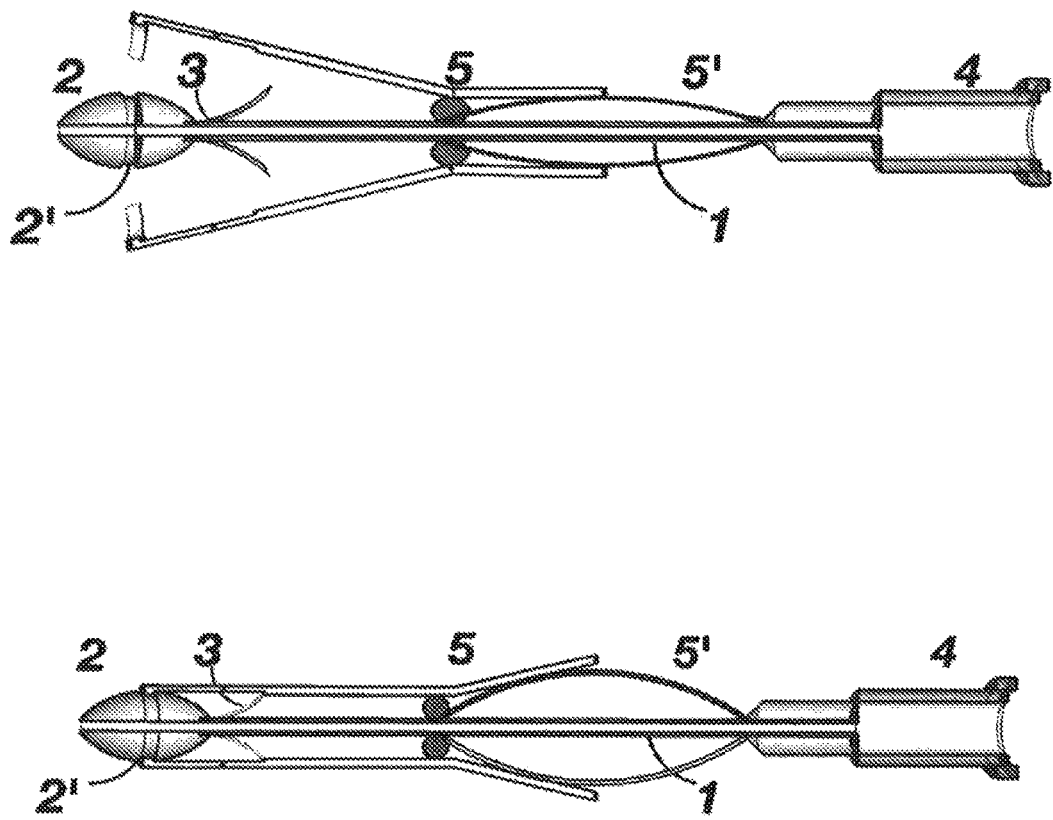
FIG. 5 shows a device wherein a circular impression (2') is made in bulbous-like body (2) wherein the spring-loaded clamp (5, 5') fits into in closed position. Upper panel shows an open clamp, lower panel shows a closed clamp.

The clamp may be positioned anywhere along the length of the cannula. It may be positioned in such a way that it protect the sharp anchors thereby preventing health care personnel from hurting themselves and preferably close in an impression (2') made in the bulbous-like body (2) as set forth in FIG. 5.

The clamp may be designed as an integrated part of the device or designed as a separate part.

According to further embodiments, the device may be designed in a case In the case the cased device is equipped with a spring-loaded clamp, the clamp may e.g. be opened and closed by pressing the sides of the case by a two fingered grip or by pushing a button according to well-known art. Preferred size of the device may be a length of about 8 cm, a width of about 3-4 cm and a height of about 2 cm is suitable. A device having a length of about 4 cm, a width of about 2 cm and a height of about 1 cm is also suitable. Any dimensions within said ranges are also suitable.

Figure 6:
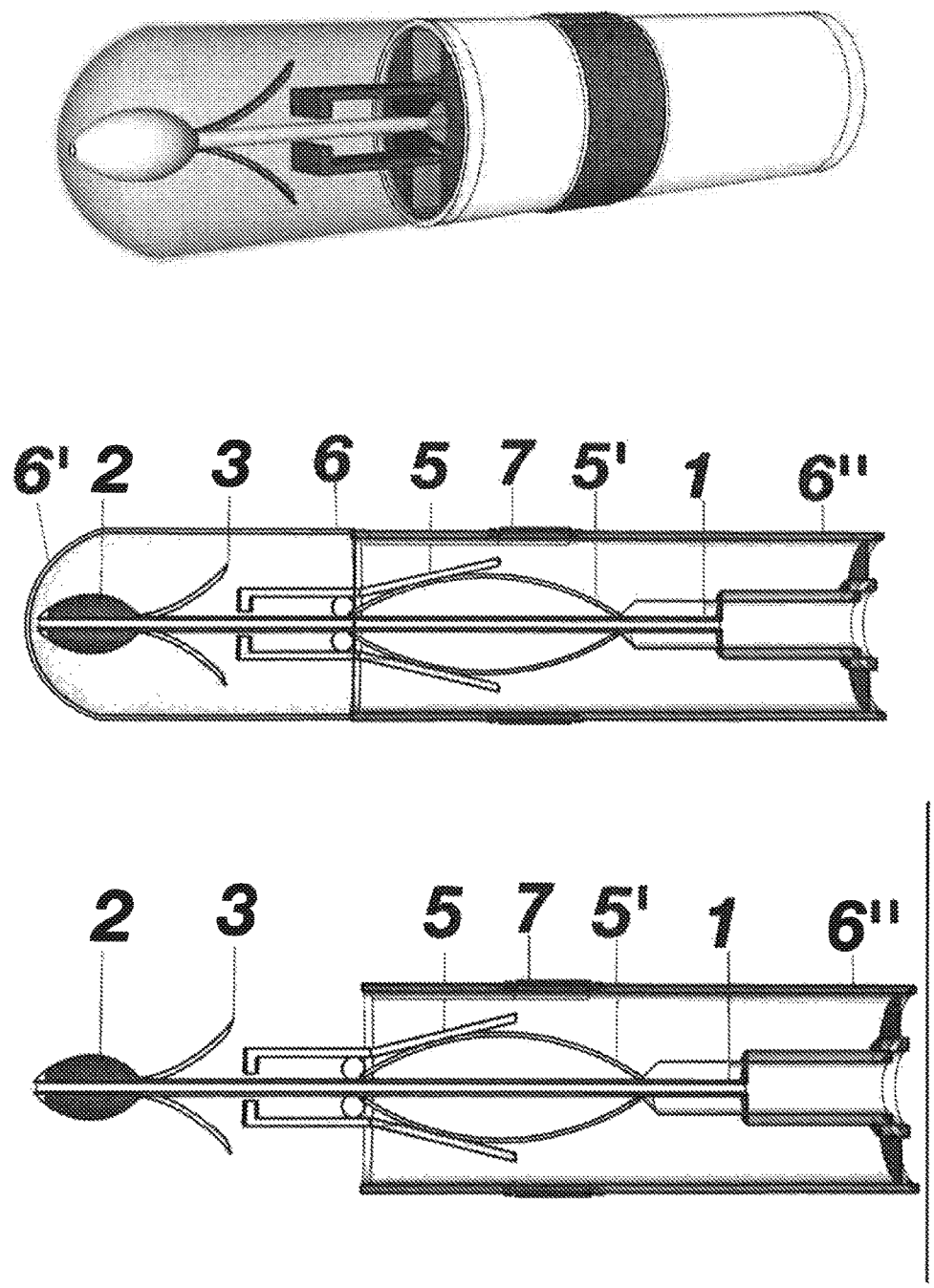
FIG. 6 shows a cased (6) spring-loaded device according to the invention. The cannula (1) with the bulbous-like body (2) and anchors (3) are covered by a removable cap (6') and the spring-loaded (5') clamp (5) is opened and closed by pushing button (7). The rest of the case (6") serves also as a holding means. Upper panel shows a three dimensional view of the cased device; middle panel shows a cross section of the cased device and lower panel shows a cross section of a cased device wherein the cap (6') has been removed and the device is ready for use.

A cased (6) spring-loaded device is illustrated in FIG. 6. The cannula (1) with the bulbous-like body (2) and anchors (3) are covered by a cap (6') and the spring-loaded (5') clamp (5) is opened and closed by pushing button (7). The rest of the case (6") serves also as a holding means. The cap may be removed or slide to uncover/cover the bulbous-like body and anchors.

It is expedient that the device according to the invention is made as a disposable device, but this is not essential.

In another aspect, the present invention is related to a process for introducing and maintaining a port in an umbilical vessel comprising utilizing a forceps to open or stretch apart the open entrance to an umbilical vessel, and inserting the device according to the invention in said umbilical vessel.

In yet another aspect, the present invention is related to a kit for umbilical vessel catheterization, comprising a forceps to open or stretch apart the open entrance to an umbilical vessel, device according to the invention, and catheter or syringe for connecting to said device for fluids or medicaments to be infused or blood samples to be taken. The kit may comprise both catheters and syringes. Preferably, the kit is sterilized.

Use of a kit according to the invention for catheterization of an umbilical vein and infusion of fluids or medicaments via the umbilical vein are thus encompassed by the present invention.

Use of a kit according to the invention for catheterization of an umbilical artery and aspiration of blood from an umbilical artery are thus encompassed by the present invention.

The procedure for injection and/or infusion of fluids and medicaments or aspiration of blood may be automatized.

The invention claimed is:

1. A device for introducing and maintaining a port in an open entrance of an umbilical vessel of a mammalian neonate, comprising a cannula equipped with a bulbous-like body at the distal end, one or more anchors configured to attach the device to the vessel, a connecting part for connecting catheters, and syringes in the proximal end, wherein said one or more anchors branches off from the cannula, extends along the cannula, and curves back into a hook member.

2. Device according to claim 1, wherein said one or more anchors is placed at or near the proximal basis of said bulbous-like body.

3. Device according to claim 1, wherein said one or more anchors is placed anywhere along the length of the cannula.

4. Device according to claim 1, wherein the external diameter of the cannula is expanded over a portion of the cannula in the region wherein the free end of the hook member abut the transition region between the expanded and non-expanded portion.

5. Device according to claim 1, wherein the device is further equipped with a locking ring to be moved forward and lock said one or more anchors.

6. Device according to claim 1, wherein said device is equipped with a spring-loaded clamp configured to close the umbilical cord.

7. Device according to claim 6, wherein the spring-loaded clamp closes in an impression made in the bulbous-like body.

8. A device for introducing and maintaining a port in an open entrance of an umbilical vessel of a mammalian neonate, comprising a cannula equipped with a bulbous-like body at the distal end, one or more anchors configured to attach the device to the vessel, a connecting part for connecting catheters, and syringes in the proximal end, wherein said one or more anchors branches off from the cannula, wherein said bulbous-like body and said one or more anchors are configured as an integrated body.

* * * * *